United States Patent
Almulhim

(10) Patent No.: US 12,220,111 B1
(45) Date of Patent: Feb. 11, 2025

(54) LAPAROSCOPIC SURGICAL DRAIN AND LAPAROSCOPE

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/377,657

(22) Filed: Oct. 6, 2023

(51) Int. Cl.
*A61B 1/313* (2006.01)
*A61M 27/00* (2006.01)

(52) U.S. Cl.
CPC ........... *A61B 1/3132* (2013.01); *A61M 27/00* (2013.01)

(58) Field of Classification Search
CPC ......... A61B 90/00; A61B 34/20; A61B 17/02; A61B 1/3132; A61B 1/313; A61B 1/00; A61M 27/00; A61M 1/90
See application file for complete search history.

(56) References Cited

U.S. PATENT DOCUMENTS

| | | | |
|---|---|---|---|
| 5,152,772 A | 10/1992 | Sewell et al. | |
| 5,891,111 A | 4/1999 | Ismael | |
| 2004/0230179 A1 | 11/2004 | Shehada | |
| 2005/0004536 A1* | 1/2005 | Opie | A61M 27/00 604/317 |
| 2022/0240961 A1 | 8/2022 | Kao et al. | |
| 2023/0080646 A1 | 3/2023 | Jain | |
| 2023/0117754 A1* | 4/2023 | Kim | A61B 1/00195 600/106 |

OTHER PUBLICATIONS

A. Chak, "Sedationless upper endoscopy",https://www.semanticscholar.org/paper/Sedationless-upper-endosco.-Chak-Rothstein/175ca9d0d8d26732986e5b37b40318d94bb5c87b> 2006. (Year: 2006).*
French catheter (Fr) conversion to mm <https://www.convert-me.com/en/convert/wire_gauge/gaugeFCS.html?u=gaugeFCS&v=11#google_vignette> (Year: 2024).*
A. Chak, "Sedationless upper endoscopy",https://www.semanticscholar.org/paper/Sedationless-upper-endoscopy.-Chak-Rothstein/175ca9d0d8d26732986e5b37b40318d94bb5c87b> 2006. (Year: 2006).*
Difference Between Endoscopy and Laparoscopy "http://www.differencebetween.net/science/health/difference-between-endoscopy-and-laparoscopy-2/" (Year: 2024).*
Mercy Health Endoscopic and Laparoscopic Surgery "https://www.mercy.com/health-care-services/general-surgery/specialties/endoscopic-laparoscopic-surgery" (Year: 2024).*

* cited by examiner

*Primary Examiner* — Guy K Townsend
*Assistant Examiner* — Gabriella E Burnette
(74) *Attorney, Agent, or Firm* — Nath, Goldberg & Meyer; Joshua B. Goldberg

(57) ABSTRACT

A laparoscopic surgical device includes a drain tube having a first drain end and a second drain end. The drain tube has a diameter of 2 mm to 5 mm. A laparoscope tube having a diameter of 5 mm is located adjacent to the drain tube. The laparoscope tube has a fixed end and a free end. The drain tube functions as a surgical drain and the laparoscope tube provides an access path into a surgical site for a camera or tools for surgery.

9 Claims, 1 Drawing Sheet

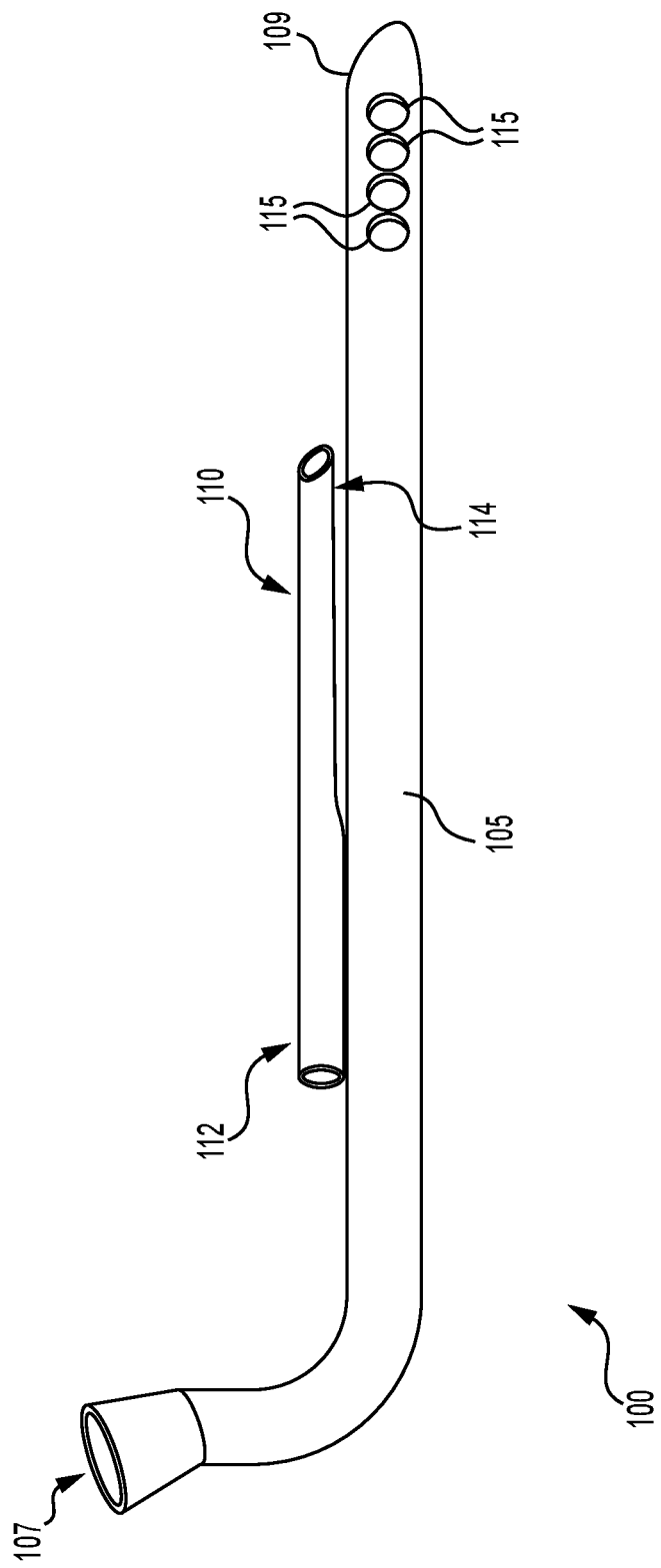

LAPAROSCOPIC SURGICAL DRAIN AND LAPAROSCOPE

BACKGROUND

1. Field

The present disclosure relates to surgical devices, and particularly to a laparoscopic surgical drain and laparoscope.

2. Description of the Related Art

Surgical procedures in the abdomen often require incisions to access internal organs. These incisions are often quite large and are prone to leave scars. In some case, multiple incisions are needed to insert a camera and other surgical tools.

In general, a laparoscopic tube is used for surgical procedures in the abdomen. Multiple tubes are necessary in some instances.

Accordingly, there is a need for new surgical devices addressing these needs.

SUMMARY

Ordinary laparoscopic tubes are large necessitating a large incision and prone to leaving a large scar. There is a need for a small laparoscopic surgical device that will only require a small incision in the abdomen.

A surgical device, in one embodiment, includes a drain tube having a first drain end and a second drain end. The drain tube can have a diameter of about 2 mm to about 5 mm. A laparoscope tube is located adjacent to the drain tube and has a fixed end and a free end. The drain tube functions as a surgical drain and the laparoscope tube provides an access path into a surgical site.

In certain embodiments, the laparoscope tube can be small and can have a diameter of about 5 mm, allowing for a camera or surgical tools to pass through.

The free end of the laparoscopic tube can be flexibles allowing for easy movement of a camera or surgical tools.

The second drain end can include multiple openings.

The second drain end and the free end of the laparoscopic tube can be positioned to extend into the surgical site.

A laparoscopic surgical device, in an alternate embodiment, can include a drain tube having a first drain end and a second drain end. The drain tube can have a diameter of about 2 mm to about 5 mm. A laparoscope tube having a diameter of about 5 mm can be located adjacent to the drain tube. The laparoscope tube can have a fixed end and a free end. The drain tube csn function as a surgical drain and the laparoscope tube can provide an access path into a surgical site.

The free end of the laparoscopic tube can be flexible.

The second drain end can include multiple openings.

The second drain end and the free end of the laparoscope tube can be positioned to extend into the surgical site.

These and other features of the present subject matter will become readily apparent upon further review of the following specification.

BRIEF DESCRIPTION OF THE DRAWINGS

The sole drawing FIGURE shows an illustration of a laparoscopic surgical device.

Similar reference characters denote corresponding features consistently throughout the attached drawings.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats, and the like.

"Patient" as used herein refers to a subject in need of treatment of a condition, disorder, or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques. A surgical device used for open and laparoscopic surgeries includes a surgical drain and a laparoscope tube. The laparoscopic tube provides an access path into a surgical site to help with visual diagnosis obviating the need to re-open a patient.

The FIGURE presented herein is an illustration of a laparoscopic surgical device 100 that includes a drain tube 105 having a first drain end 107 and a second drain end 109. The drain tube 105 has a small diameter of about 2 mm to about 5 mm allowing for use on a patient of any age and body size. A laparoscope tube 110 is located adjacent to the drain tube 105 and has a fixed end 112 and a free end 114. The drain tube 105 functions as a surgical drain and the laparoscope tube 110 provides an access path into a surgical site allowing a camera or surgical tools to pass therethrough. The laparoscopic tube 110 can be utilized, if needed, in post-surgical procedures.

The laparoscope tube 110 should be small and in some cases can have a diameter of about 5 mm.

The free end 114 of the laparoscopic tube 110 can be flexible allowing for easy movement of a camera or surgical tools inserted through the laparoscopic tube 110.

The second drain end 109 can include multiple openings 115.

The second drain end 109 and the free end 114 of the laparoscopic tube 110 are positioned to extend into the surgical site.

The laparoscopic surgical device 100 is a simple, small surgical drain that includes an additional laparscope tube 110 that can be used for open and lapaoscpic surgeries. It can be used for a patient of any age or body size. The laparoscopic tube 110 can be used for a camera or surgical tools, and can be used for post-surgical procedures. The size of the surgical device 100 is such that only a small minimal incision is needed in operation, leaving little or no scaring.

It is to be understood that the laparoscopic surgical device is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A surgical device, comprising:
    a drain tube having a first drain end and a second drain end, the drain tube having a diameter of about 2 mm to about 5 mm; and
    a laparoscope tube located adjacent to the drain tube, the laparoscope tube having a fixed end and a free end;
    wherein the drain tube functions as a surgical drain and the laparoscope tube provides an access path into a surgical site, and
    wherein the laparoscope tube is sized to be shorter than the drain tube such that the fixed end of the laparoscope tube is coupled to the drain tube while the free end of the laparoscope tube is uncoupled from the drain tube.

2. The surgical device as recited in claim 1, wherein the laparoscope tube has a diameter of about 5 mm.

3. The surgical device as recited in claim 1, wherein the free end of the laparoscopic tube is flexible.

4. The surgical device as recited in claim 1, wherein the second drain end includes multiple openings.

5. The surgical device as recited in claim 1, wherein the second drain end and the free end of the laparoscopic tube are configured to be positioned to extend into the surgical site.

6. A laparoscopic surgical device, comprising:
    a drain tube having a first drain end and a second drain end, the drain tube having a diameter of about 2 mm to about 5 mm; and
    a laparoscope tube having a diameter of about 5 mm located adjacent to the drain tube, the laparoscope tube having a fixed end and a free end;
    wherein the drain tube functions as a surgical drain and the laparoscope tube provides an access path into a surgical site, and
    wherein the laparoscope tube is sized to be shorter than the drain tube such that the fixed end of the laparoscope tube is coupled to the drain tube while the free end of the laparoscope tube is uncoupled from the drain tube.

7. The laparoscopic surgical device as recited in claim 6, wherein the free end of the laparoscopic tube is flexible.

8. The laparoscopic surgical device as recited in claim 6, wherein the second drain end includes multiple openings.

9. The laparoscopic surgical device as recited in claim 6, wherein the second drain end and the free end of the laparoscope tube are configured to be positioned to extend into the surgical site.

* * * * *